(12) United States Patent
Que et al.

(10) Patent No.: US 11,947,195 B2
(45) Date of Patent: Apr. 2, 2024

(54) CONTACT LENS INCLUDING NANOPORES

(71) Applicant: Iowa State University Research Foundation, Inc., Ames, IA (US)

(72) Inventors: Long Que, Silcon Valley, CA (US); Gil Ben-Shlomo, Ames, IA (US); Chao Song, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 348 days.

(21) Appl. No.: 17/051,665

(22) PCT Filed: Nov. 20, 2018

(86) PCT No.: PCT/US2018/061915
§ 371 (c)(1),
(2) Date: Oct. 29, 2020

(87) PCT Pub. No.: WO2020/076349
PCT Pub. Date: Apr. 16, 2020

(65) Prior Publication Data
US 2021/0311329 A1    Oct. 7, 2021

Related U.S. Application Data

(60) Provisional application No. 62/743,779, filed on Oct. 10, 2018.

(51) Int. Cl.
| | |
|---|---|
| *G02C 7/04* | (2006.01) |
| *A61B 3/16* | (2006.01) |
| *A61B 5/00* | (2006.01) |
| *A61B 5/145* | (2006.01) |
| *A61B 90/00* | (2016.01) |
| *A61F 9/00* | (2006.01) |
| *G02B 1/04* | (2006.01) |
| *G02B 1/10* | (2015.01) |

(52) U.S. Cl.
CPC ............... *G02C 7/049* (2013.01); *A61B 3/16* (2013.01); *A61B 5/14507* (2013.01); *A61B 5/4839* (2013.01); *A61B 5/6821* (2013.01); *A61B 90/39* (2016.02); *A61F 9/0008* (2013.01); *G02B 1/043* (2013.01); *G02B 1/10* (2013.01); *A61F 2250/0024* (2013.01); *A61F 2250/0097* (2013.01)

(58) Field of Classification Search
None
See application file for complete search history.

(56) References Cited

U.S. PATENT DOCUMENTS

| | | |
|---|---|---|
| 2010/0113901 A1 | 5/2010 | Zhang et al. |
| 2017/0042480 A1 | 2/2017 | Gandhi et al. |

FOREIGN PATENT DOCUMENTS

| | | |
|---|---|---|
| CN | 108095886 A | 6/2018 |
| WO | WO-2020076349 A1 | 4/2020 |

OTHER PUBLICATIONS

"International Application Serial No. PCT/US2018/061915, International Search Report dated Jul. 8, 2019", 5 pgs.
"International Application Serial No. PCT/US2018/061915, Written Opinion dated Jul. 8, 2019", 6 pgs.
Araci, Ismail E., "An implantable microfuidic device for self-monitoring of intraocular pressure", nature medicine, vol. 20, No. 9—Technical Reports, (Sep. 2014), 1074-1080.
Chen, Po-Jui, et al., "Imlantable Parylene-Based Wireless Intraocular Pressure Sensor", MEMS 2008, Tucson, AZ, USA, Jan. 13-17, 2008, (2008), 58-61.
Creech, J. L., et al., "Dispersive Mixing in the Posterior Tear Film Under a Soft Contact Lens", Ind. Eng. Chem. Res. 2001, 40, 3015-3026, (201), 3015-3026.
Firat, P G. et al., "The influence of soft contact lenses on the intraocular pressure measurement", Eye (2012) 26, 278-282, (2012), 278-282.
Gupta, Himanshu, et al., "Contact lenses in ocular therapeutics", Drug Discovery Today, vol. 17, Nos. 9/10, May 2012, (2012), 522-527.
Haque, R. M., et al., "A 3D Implantable Microsystem for Intraocular Pressure Monitoring using a Glass-In-Silicon Reflow Process", MEMS 2011, Caneun, Mexico, Jan. 23-27, 2011, (2011), 995998.
Kouhani, Mohammad Hossein Mazaheri, et al., "Wireless Intraocular Pressure Sensor Using Stretchable Variable Inductor", MEMS 2017, Las Vegas, NV, USA, Jan. 22-26, 2017, (2017), 557-560.
Leonardi, Matteo, et al., "Wireless contact lens sensor for intraocular pressure monitoring: assessment on enucleated pig eyes", Acta Ophthalmologica 2009, (2009), 433-437.
Li, Chi-Chung, et al., "Modeling Ophthalmic Drug Delivery by Soaked Contact Lenses", Ind. Eng. Chem. res. 2006, 45, 3718-3734, (2006), 3718-3734.
Peng, Cheng-Chun, et al., "Drug Delivery by Contact Lens in Spontaneously Glaucomatous Dogs", Current Eye Research 37(3), 204-211, 2012, (2012), 204-211.
Peng, Cheng-Chun, et al., "Extended drug delivery by contract lenses for glaucoma therapy", Journal of Controlled Release 162 (2012) 152-158, (2012), 152-158.
Rathore, K. S., et al., "An Insight into Ophthalmic Drug Delivery System", International Journal of Pharmaceutical Sciences and Drug Research, I(1): 1-5, (2009), 1-5.
Song, Chao, et al., "A Flexible Nanopore Thin-Film-Enabled Device for Pressure Sensing and Drug Release", IEE Transactions on Nanotechnology, vol. 17, No. 5, (Sep. 2018), 962-967.
Song, Chao, et al., "High-resolution, flexible, and transparent nanopore thin film sensor enabled by cascaded Fabry-Perot effect", Optics Letters, vol. 43, No. 13, (2018), 3057-3060.

(Continued)

*Primary Examiner* — Jennifer Chin
(74) *Attorney, Agent, or Firm* — Schwegman Lundberg & Woessner, P.A.

(57) ABSTRACT

Various embodiments disclosed relate to contact lens including nanopores. A contact lens can include a nanoporous film including nanopores that are on an inner surface of the contact lens, and a backing lens on the nanoporous film. Various embodiments further include a biomarker-sensing region of the nanoporous film, a drug storage and delivery region of the nanoporous film, or a combination thereof.

18 Claims, 6 Drawing Sheets

(56) References Cited

OTHER PUBLICATIONS

Yan, J, et al., "An Unpowered, Wireless Contact Lens Pressure Sensor for Point-of-Care Giaucoma Diagnosis", Engineering in Medicene and Biology Society, EMBC, 2011 Annual International Conference of the IEEE,. (Aug. 30, 2011), 2522-2525.

"International Application Serial No. PCT/US2018/061915, International Preliminary Report on Patentability dated Apr. 22, 2021", 8 pgs.

CONTACT LENS INCLUDING NANOPORES

CROSS-REFERENCE TO RELATED APPLICATION

This application is a U.S. National Stage Filing under 35 U.S.C. 371 from International Application No. PCT/US2018/061915, filed 20 Nov. 2018, and published as WO 2020/076349 on 16 Apr. 2020, which application claims the benefit of priority to U.S. Provisional Patent Application Ser. No. 62/743,779 filed Oct. 10, 2018, the disclosure of which are incorporated herein in their entirety by reference.

BACKGROUND

Glaucoma, a leading cause of blindness worldwide, is expected to affect about 80 million people by 2023. Elevated IOP is a primary contributing factor to this disease, its measurements are used for glaucoma diagnosis and patient monitoring. The IOP can fluctuate highly, and occasional IOP measurements in the clinician's office are not always sufficient to manage glaucoma.

Recently, the FDA has approved marketing of Triggerfish® "smart" contact lens sensor to monitor IOP, which includes strain gauges that generate signals that can be translated into eye pressure or change of eye pressure. The IOP data is transmitted from the lens wirelessly to a small adhesive antenna placed on the face near the eye. The antenna then transmits the data to a portable recorder worn by the patient. However, the fabrication and operation of this and other TOP sensors are complicated.

Conventional IOP sensors cannot deliver a drug for treatment of glaucoma. Drug delivery is a difficult task in ocular therapeutics due to the physiological and anatomical constraints of the eye. The correct therapeutic concentration of a drug at the required site of action is difficult to obtain. This has led to clinicians recommending frequent topical dosing, resulting in noncompliance by patients and decreased cost-effectiveness. Further, less than 1% of a topically administered drug typically reaches the aqueous humor.

Current glaucoma screening techniques including IOP measurement have poor sensitivity and are unable to diagnose early primary glaucoma. Biomarkers such as cytokines are believed to be involved in oxidative stress and inflammation and can serve as a biomarker indicating early glaucoma. However, in order to measure, screen and validate glaucoma biomarkers, tear films have to be first obtained from the recruited patients and then analyzed using a high-sensitivity enzyme-linked immunosorbent assay (ELISA), which is an inconvenient and expensive procedure.

SUMMARY OF THE INVENTION

Various embodiments of the present invention provides a contact lens. The contact lens includes a nanoporous film that includes nanopores that are on an inner surface of the contact lens. The contact lens also includes a backing lens on the nanoporous film.

Various embodiments of the present invention provide a contact lens that includes a nanoporous film including nanopores that are on an inner surface of the contact lens and that are orthogonally-oriented with respect to the inner surface of the contact lens. The nanoporous film includes anodic aluminum oxide (AAO) on the inner surface of the contact lens. The contact lens includes a backing lens on the nanoporous film that is configured to hold the nanoporous film against an eye wearing the contact lens. The backing lens includes polydimethylsiloxane (PDMS).

Various embodiments of the contact lens include a biomarker-sensing region. The biomarker-sensing region of the nanoporous film includes antibodies absorptive toward a biomarker on the inner surface of the contact lens. In some embodiments, the biomarker-sensing portion of the nanoporous film is functionalized with human IL-12p70 antibody, and the biomarker-sensing portion of the nanoporous film reflects light with a shift in wavelength that correlates to a degree of loading of cytokines IL-12p70 on the antibodies.

Various embodiments of the contact lens includes a drug-storage region. In the drug-storage region, at least some of the nanopores in the nanoporous film include a drug therein, such as timolol.

Various embodiments provide a method of using the contact lens in a wearer's eye. The method includes exposing the contact lens to a light source. The method includes measuring wavelength and intensity of light from the light source reflected from the contact lens in the wearer's eye. The method includes determining intraocular pressure (IOP) from the wavelength and intensity of light measured.

Various embodiments provide a method of using the contact lens including a biomarker-sensing region in a wearer's eye. The method includes exposing the contact lens to a light source. The method includes measuring wavelength and intensity of light from the light source reflected from the contact lens in the wearer's eye. The method also includes determining glaucoma biomarker concentration or change in concentration from the wavelength and intensity of light measured.

Various embodiments provide a method of using the contact lens including a drug-storage region. The method includes providing the drug to the wearer's eye from the nanopores of the contact lens in the wearer's eye.

Various embodiments provide a method of making the contact lens. The method includes placing the nanoporous film on the backing lens, to form the contact lens.

Various embodiments provide a method of making the contact lens. The method includes forming anodic aluminum oxide (AAO) on a glass substrate. The method includes curing a polydimethylsiloxane (PDMS) film on the AAO, to form an AAO/PDMS composite film. The method includes removing the AAO/PDMS composite film from the glass substrate. The method also includes placing the AAO/PDMS composite film on a backing lens, to form the contact lens.

In various embodiments, the contact lens of the present invention and methods of using the same have certain advantages over other contact lenses and over other methods of IOP monitoring, ocular drug delivery, biomarker detection, or a combination thereof, at least some of which are unexpected. For example, in various embodiments, the contact lens of the present invention can monitor IOP in real-time, providing a more convenient and faster method of detecting IOP than conventional methods that require a patient to visit a clinician's office. In various embodiments, a patient or medical professional can repeatedly, at any desired time, in any environment including outside of a clinic, measure IOP using the contact lens of the present invention, and can avoid the use of specialized, expensive tonometry equipment that requires training and expertise. In various embodiments, the contact lens of the present invention can be fabricated more easily than other IOP sensors and can have a more simple construction. In various embodiments, the contact lens of the present invention can measure IOP without metal strain gauges, providing simpler operation and construction than other IOP measuring devices. In various embodiments, the contact lens of the present invention can be free of a power supply and can be used to measure IOP without any forms of powered data transfer between the contact lens and another device, providing a simpler way to measure IOP than other devices.

In various embodiments, the contact lens of the present invention can deliver one or more drugs to the eye, providing more convenient drug delivery than conventional topical administration such as eye-drops. In various embodiments, by releasing drugs directly into the eye from the contact lens, the contact lens of the present invention can provide a more accurate drug dose than conventional topical administration such as via eye-drops. In various embodiments, drug delivery from the contact lens of the present invention can provide a more efficient delivery of the drug with a greater proportion of the administered drug being absorbed in a therapeutically-useful manner by the eye than convention topical administration of drugs. In various embodiments, drug delivery from the contact lens of the present invention can provide more efficient delivery of drugs to the eye such that a larger proportion of the administered. In various embodiments, the contact lens of the present invention can reduce or eliminate the need for conventional topical administration of drugs such as via eye drops, and can provide extended and more accurate dosing of drugs to the eye. In various embodiments, drug delivery from the contact lens of the present invention can be less expensive and simpler than other alternatives to conventional topical administration of drugs.

In various embodiments, the contact lens of the present invention can detect biomarkers of various diseases, including diseases of the eye (e.g., glaucoma, inflammatory diseases such as keratitis and uveitis, keratoconjunctivitis sicca, intra-ocular or extraocular infection, ulcerative keratitis, indolent/non-healing ulcer, or ocular adnexal disease) providing a more convenient method of detecting biomarkers than conventional methods such as collection of tear films and ELISA screening thereof. In various embodiments, detecting biomarkers using the contact lens of the present invention can be less expensive and faster than conventional biomarker detection methods, can be performed in real-time, and can be performed without a trip to the clinic.

In various embodiments, the contact lens of the present invention can provide two or all of IOP sensing, ocular drug delivery, and biomarker detection in a single contact lens device. In various embodiments, by combining two or more of these features, the contact lens of the present invention provides enhanced convenience over other ocular disease maintenance devices and methods. By combining two or more of these features, the contact lens of the present invention can provide better diagnosis and maintenance of ocular diseases as compared to conventional treatment methods. In various embodiments, the contact lens of the present invention can be easier to fabricate and more convenient to use than other devices that combine two of more of these features.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1A:
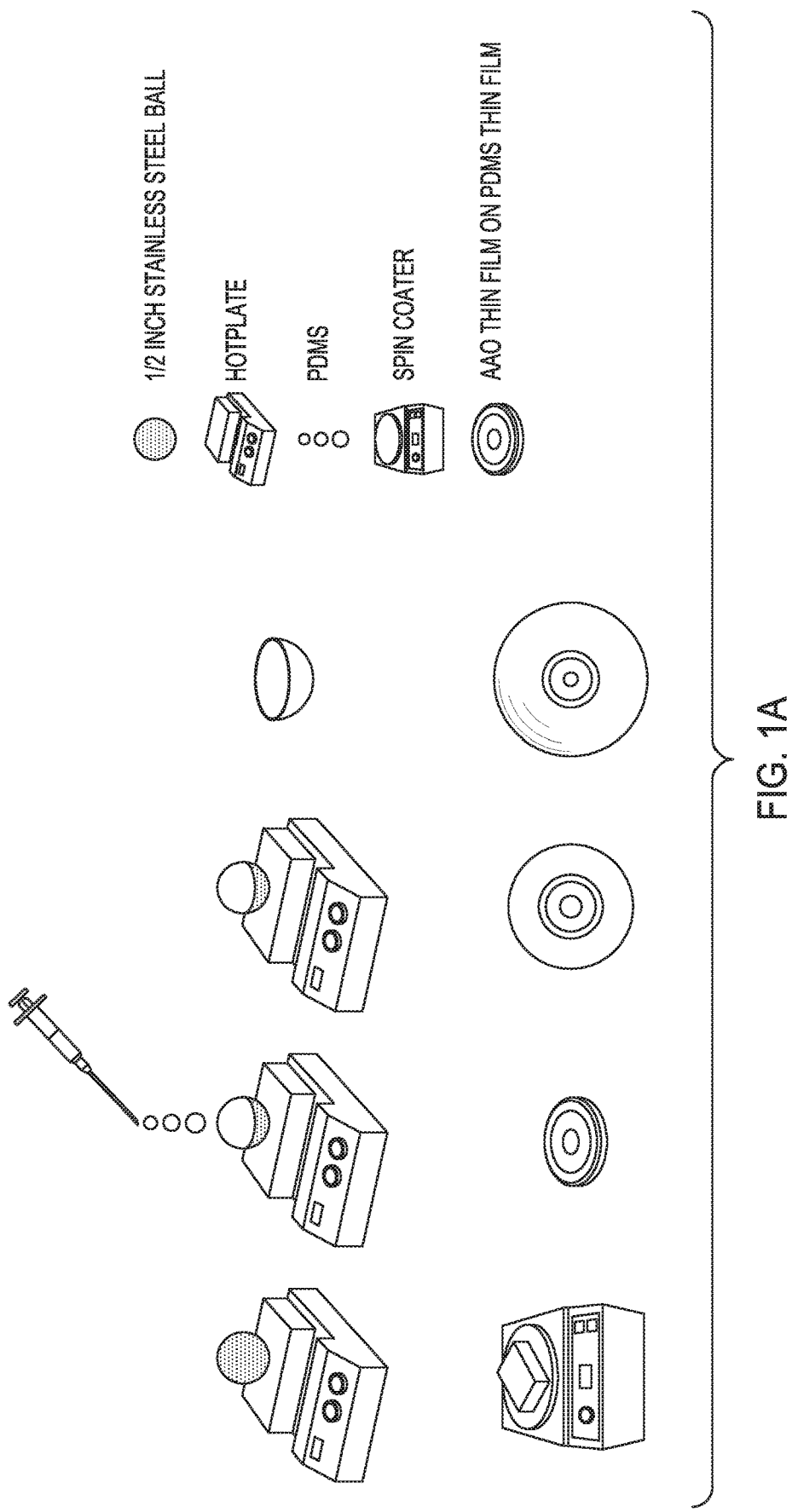
FIG. 1A illustrates backing lens fabrication, in accordance with various embodiments.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y. or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B. or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl $(C_1)$, ethyl $(C_2)$, propyl $(C_3)$, or butyl $(C_4)$, and $(C_0-C_b)$hydrocarbyl means in certain embodiments there is no hydrocarbyl group.

As used herein, the term "polymer" refers to a molecule having at least one repeating unit and can include copolymers.

Contact Lens.

Various embodiments provide a contact lens. The contact lens includes a nanoporous film including nanopores. The nanopores are on an inner surface of the contact lens, which is the concave side of the contact lens that is designed to contact the outside of the eye of a wearer of the contact lens. The contact lens includes a backing lens on the nanoporous film. The backing lens is on the outer surface of the contact lens, which is the convex side of the contact lens that is designed to face outward from the eye of a wearer of the contact lens. The contact lens can be designed for use with a human or animal.

The backing lens can have any suitable shape or diameter, such that the contact lens functions as described herein. The backing lens can have a circular shape with a diameter designed to fit the user's eye, such as the shape of a conventional contact lens. The nanoporous film can have any suitable shape, such as a shape that is the same or different as the shape of the backing. The nanoporous film can have a circular shape, or the nanoporous film can have a polygonal shape or an irregular shape. In some embodiments, the nanoporous film can have a largest dimension equal to or less than the diameter of the backing, which can allow the backing lens to contact the eye of the wearer and to hold the thin nanoporous film against the eye. The nanoporous film can be substantially optically transparent to the eye of the wearer. In some embodiments, the backing lens can provide vision correction to the eye of the wearer.

The nanoporous film can cover any suitable proportion of the surface area of the inner surface of the backing lens, such as about 1% to about 100%, or about 5% to about 80%, or about 1% or less, or less than, equal to, or greater than about 5%, 10, 15, 20, 25, 30, 35, 40, 45, 50, 55, 60, 65, 70, 75, 80, 85, 90, 95% or more, or about 100%

The nanopores can have any suitable orientation in the contact lens (i.e., the orientation of the longitudinal axis of the nanopores), such that the contact lens can be used as described herein. The nanopores can be orthogonally-oriented with respect to the inner surface and outer surface of the contact lens. In some embodiments, at least some of the nanopores can have open ends that open to the inner surface of the contact lens, such as less than, equal to, or greater than about 1% of the nanopores, 2, 3, 4, 5, 6, 8, 10, 15, 20, 25, 50, 75, 80, 85, 90, 92, 94, 95, 96, 97, 98, 99, or about 100% of the nanopores. In other embodiments, at least some of the openings of the nanopores facing the inner surface of the contact lens can be plugged or covered with another material, such as less than, equal to, or greater than about 1% of the nanopores, 2, 3, 4, 5, 6, 8, 10, 15, 20, 25, 50, 75, 80, 85, 90, 92, 94, 95, 96, 97, 98, 99, or about 100% of the nanopores. The other ends of the nanopores, opposite the open ends, can be closed, with the nanopores terminating at or prior to reaching the backing lens, such as at a backing layer contacting the ends of the nanopores. Any suitable proportion of the surface area of the inner surface of the nanoporous film can be covered with the nanopores, such as about 1% to about 100%, or about 20% to about 95%, or about 1% or less, or less than, equal to, or greater than about 5%, 10, 15, 20, 25, 30, 35, 40, 45, 50, 55, 60, 65, 70, 75, 80, 85, 90, 95, or about 100%.

The nanopores can have any suitable cross-sectional profile perpendicular to the longitudinal axis of the pores. For example, the nanopores can be circular, polygonal, or irregular in shape. In some embodiments, the nanopores are hexagonal in shape.

The nanoporous film can include a nanoporous layer wherein the nanopores are formed. The nanopores in the nanoporous film can be formed in any suitable material, such as a metal, a metal oxide, or a combination thereof. The metal can be any suitable metal, such as silicon or nickel. In some embodiments, the nanopores can be formed in aluminum oxide, or anodic aluminum oxide (AAO). AAO is a self-organized material with honeycomb-like structure formed by high density arrays of uniform and parallel pores. The nanoporous film can further include a backing layer on the opposite side of the nanopores from the inner surface of the contact lens. The backing layer can be on the same side of the nanopores as the backing lens, and in some embodiments the backing layer can contact the backing lends. The backing layer can cover the nanopores such that one end of the nanopores are closed. The backing layer can be formed of any suitable material, such as a material the same, similar to, or different than the backing lens. The backing layer can include polydimethylsiloxane (PDMS), poly(ethylene glycol) methacrylate (PEGMA), or a combination thereof. The backing layer can include polydimethylsiloxane (PDMS).

The nanoporous film can have any suitable overall thickness, such as about 1 micron to about 150 microns, or about 20 microns to about 45 microns, or about 1 micron or less, or less than, equal to, or greater than about 2 microns, 3, 4, 5, 6, 8, 10, 12, 14, 16, 18, 20, 22, 24, 26, 28, 30, 32, 34, 36, 38, 40, 42, 44, 45, 46, 48, 50, 55, 60, 70, 80, 90, 100, 110, 120, 130, 140, or about 150 microns or more. The nanoporous layer can be thinner or thicker than the backing layer. The nanoporous layer can have any suitable thickness, such as about 0.1 micron to about 10 microns, about 1 micron to about 3 microns, or about 0.1 micron or less, or less than, equal to, or greater than about 0.5 microns, 1 micron, 1.5, 2, 2.5, 3, 4, 5, 6, 7, 8, 9, or about 10 or more. The backing layer can have any suitable thickness, such as about 1 micron to about 100 microns, about 20 microns to about 40 microns, or about 1 micron or less, or less than, equal to, or greater than about 2, 3, 4, 5, 6, 8, 10, 12, 14, 16, 18, 20, 22, 24, 26, 28, 30, 32, 34, 36, 38, 40, 42, 44, 46, 48, 50, 55, 60, 70, 80, 90, or about 100 microns or more.

The nanopores in the nanoporous film can have any suitable depth. In some embodiments, the depth of the nanopores is equal to the depth of the layer of material that the nanopores are formed in (i.e. the nanoporous layer). In various embodiments, the nanopores have a depth of about 0.1 micron to about 10 microns, about 1 micron to about 3 microns, or about 0.1 micron or less, or less than, equal to, or greater than about 0.5 microns, 1 micron, 1.5, 2, 2.5, 3, 4, 5, 6, 7, 8, 9, or about 10 or more. The nanopores in the nanoporous film can have any suitable diameter (e.g., largest dimension perpendicular to the longitudinal axis), such as about 10 nm to about 200 nm, about 30 nm to about 50 nm, or about 10 nm or less, or less than, equal to, or greater than about 20 nm, 25, 30, 32, 34, 36, 38, 40, 42, 44, 46, 48, 50, 60, 70, 80, 90, 100, 125, 150, 175, or about 200 nm or more. The nanopores in the nanoporous film can have any suitable density per surface area of the nanoporous film, such as about $10^5$ to about $10^{15}$ pores per cm$^2$, about $10^8$ to about $10^{12}$ pores per cm$^2$, or about $10^5$ pores per cm$^2$ or less, or less than, equal to, or greater than about $10^6$ pores per cm$^2$, $10^7$, $10^8$, $10^9$, $10^{10}$, $10^{11}$, $10^{12}$, $10^{13}$, $10^{14}$, or about $10^{15}$ or more.

The contact lens includes a backing lens on the nanoporous film. The backing lens can be part of or form an outer convex surface of the contact lens. The concave inner side of the backing lens can be attached to the outer side of the nanoporous film, such as via another intervening layer (e.g., adhesive or tackifier), or via direct contact between the backing lens and the nanoporous film (e.g., physical adhesion, such as including Van der Waals forces). In some embodiments, physical adhesion can be achieved by using the same or similar materials to form the backing lens and the backing layer of the contact lens.

The backing lens can be formed of any suitable material, such as the same or similar material as the backing. The backing lens can include polydimethylsiloxane (PDMS), poly(ethylene glycol) methacrylate (PEGMA), or a combination thereof. The backing lens can include Alfafilcon A, Balafilcon A, Bufilcon A, Crofilcon, Delefilcon A, Deltafilcon A, Etafilcon A, Focofilcon A, Galyfilcon A, Hefilcon A, Hefilcon B, Hefilcon C, Hilafilcon A, Hilafilcon B, Hioxifilcon A, Hioxifilcon B, Hioxifilcon D, Lidofilcon A, Lidofilcon B, Lotrafilcon A, Lotrafilcon B, Mafilcom, Methafilcon A, Methafilcon B, Narafilcon A, Narafilcon B, Nelfilcon, Nesofilcon A, Netrafilcon A, Ocufilcon B, Ocufilcon C, Ocufilcon D, Ocufilcon E, Ocufilcon F, Omafilcon A, Perfilcon A, Phemfilcon, Phemfilcon A, Polymacon, Samfilcon A, Senofilcon A, Stenfilcon A, Surfilcon A, Teflicon, Tetrafilcon A, Vasurfilcon A, Vilfilcon A, or a combination thereof. The backing lens can have any suitable thickness, such as about 50 microns to about 2 mm, about 100 microns to about 150 microns, or about 50 microns or less, or less than, equal to, or greater than about 60 microns, 70, 80, 90, 100, 110, 120, 130, 140, 150, 160, 170, 180, 190, 200, 250, 300, 350, 400, 500, 600, 700, 800, 900 microns, 1 mm, 1.1, 1.2, 1.3, 1.4, 1.5, 1.6, 1.7, 1.8, 1.9, or about 2 mm or more. The contact lens can have an overall thickness of about 50 microns to about 2,500 microns, or about 150 microns to about 170 microns, or about 50 microns or less, or less than, equal to, or greater than about 60 microns, 70, 80, 90, 100, 110, 120, 130, 140, 150, 160, 170, 180, 190, 200, 250, 300, 350, 400, 500, 600, 700, 800, 900 microns, 1 mm, 1.1, 1.2, 1.3, 1.4, 1.5, 1.6, 1.7, 1.8, 1.9, 2, 2.1, 2.2, 2.3, 2.4, or about 2.5 mm or more.

Light that is reflected from the nanopores of the contact lens can experience a shift in wavelength that correlates to an intraocular pressure of an eye wearing the contact lens. By measuring the shift in wavelength, the intraocular pressure of the eye, or the change of the intraocular pressure of the eye, can be determined. In some embodiments, a central region of the nanoporous film includes nanopores that can be used to determine the intraocular pressure.

The contact lens can include a biomarker-sensing region of the nanoporous film, which can be the same or different than portions of the nanoporous film used to determine the intraocular pressure. The biomarker-sensing region of the nanoporous film can include nanopores or can be free of nanopores. The biomarker-sensing region of the nanoporous film includes antibodies absorptive toward a biomarker on the inner surface of the contact lens. The portions of the nanoporous film including the antibodies reflect light with a shift in wavelength that correlates to a degree of loading of the biomarker on the antibodies. As a result of a biomarker binding to the antibody, the optical path difference (OPD) of the light changes, resulting in a shift in the optical signals that correlates to the amount of biomarker that binds to the antibody. The biomarker-sensing region of the nanoporous film can be the entire nanoporous film or can be only smaller region of the nanoporous film, such as on an edge region of the nanoporous film.

The detected biomarker can be indicative of a disease or condition, such as an ocular or a systemic disease, and can be expressed in the blood or tears, from electrolytes. The detected biomarker is absorbed by a biomarker that is absorptive toward that particular biomarker. In some embodiments, the biomarker is cytokines IL-12p70f, and the antibody is human IL-12p70 antibody, and biomarker-sensing portion of the nanoporous film reflects light with a shift in wavelength that correlates to a degree of loading of cytokines IL-12p70 on the antibodies.

The antibody can be functionalized to the nanoporous film on the inner surface of the contact lens in any suitable way, such as via a linker group and optionally via metal film. The antibody can be functionalized to the nanoporous film on the inner surface of the contact lens via a gold film on the nanoporous film with 1-ethyl-3-(3-dimethylaminopropyl) carbodiimide (EDC)/N-hydroxysulfosuccinimide (NHS) chemistry. EDC (1-Ethyl-3-(3-dimethylaminopropyl)-carbodiimide) is a zero-length crosslinking agent that can be used to couple carboxyl or phosphate groups to primary amines. EDC is water soluble, which allows direct bioconjugation without prior organic solvent dissolution. Additionally, an excess of reagents and by-products can be easily removed by dialysis or gel-filtration. The reactive ester that is formed could normally be rapidly hydrolyzed in aqueous solutions, but the addition of NHS stabilizes the amine-reactive intermediate by converting it to an amine-reactive NHS ester, thus increasing the efficiency of EDC-mediated coupling reactions.

In various embodiments, at least some of the nanopores in a drug-storage region of the nanoporous film include a drug therein. The drug-storage region of the nanoporous film can be the same or different than an ocular pressure sensing region or a biomarker-sensing region. The drug-storage region of the nanoporous film can be an edge region. The drug can be any suitable drug for ocular treatment, such as for treatment of glaucoma or for any other ocular disorder, such as inflammatory diseases such as keratitis and uveitis (from any etiology), keratoconjunctivitis sicca (KCS; dry eye syndrome), intra-ocular or extraocular infection, ulcerative keratitis, indolent/non-healing ulcer, or ocular adnexal disease. The drug can be a an anti-glaucoma drug, such as a prostaglandin analog, a carbonic anhydrase inhibitor, a beta-adrenergic antagonist (beta-blocker), cholinergic agonist, an alpha2-adrenergic agonist, a rho-associated protein kinase (ROCK) inhibit, or an adenosine receptor agonist. The drug can be a parasympathomimetic, a hyperosmotic agent, a steroid (e.g., prednisolone, dexamethasone, or hydrocortisone), a non-steroidal anti-inflammatory (NSAID, e.g., diclofenac, flurbiprofen, ketorolac, or bromfenac, nepafenax), an antibiotic (e.g., gentamycin, tobramycin, amikacin, neomycin, azithromycin, polymyxin B, gramicidin, ofloxacin, ciprofloxacin, chloramphenicol, trimethoprim, sulfacetamide, gatifloxacin, moxifloxacin, levofloxacin), an antiviral (e.g., cidofovir, ganciclovir, trifluridine, idoxuridine, penciclovir), another ophthalmic drug (e.g., atropine, tropicamide, phenylephrine), or a combination thereof. The drug can be latanoprost, bimatoprost, travoprost, timolol, levobutanol, betaxolol, brimonidine, pilocarpine, dorzolamide, brinzolamide, acetazolamide, demecarium bromide, netarsudil, trabodenosine, or a combination thereof. In some embodiments, the drug is timolol, a beta blocker.

In some embodiments, the nanopores including the drug can include open ends on the inner surface of the contact lens. In some embodiments, the nanopores including the drug can have a cap or plug designed to dissolve over time. The nanopores can release the drug to the eye all at once, over a short period, or over an extended release pattern.

The contact lens can include one, two, or all of pressure sensing regions, biomarker-sensing regions, and drug-storage regions.

Method of Using a Contact Lens.

Various embodiments provide a method of using an embodiment of the contact lens described herein that includes the nanoporous film including nanopores on the inner surface of the contact lens. The subject wearing the contact lens can be a human or animal. The method can include exposing the contact lens to a light source, such as an external light source placed in front of the wearer. The method can include measuring wavelength and intensity of light from the light source that is reflected from the contact lens in the wearer's eye, such as using a spectrophotometer. The method can include determining intraocular pressure (IOP) from the wavelength and intensity of light measured.

Various embodiments provide a method of using an embodiment of the contact lens that includes a biomarker-sensing region. The method includes exposing the contact lens to a light source reflected from the contact lens in the wearer's eye. The method includes determining glaucoma biomarker concentration or change in concentration from the wavelength and intensity of light measured.

Various embodiments provide a method of using an embodiment of the contact lens that includes a drug-storage region. The method includes providing the drug to the wearer's eye from the nanopores of the contact lens in the wearer's eye.

Method of Making a Contact Lens.

Various embodiments provide a method of making an embodiment of the contact lens described herein. The method can include placing a nanoporous film on a backing lens, to form the contact lens.

The method can optionally include forming the nanoporous film, which can be formed in any suitable way. The method can include forming a nanoporous layer including the nanopores on a flat substrate, such as glass or another substrate suitable for forming the nanoporous layer. The method can include placing a backing layer on the nanoporous layer, to form a nanoporous film including the nanoporous layer and the backing layer. The method can include removing the nanoporous film.

In some embodiments, the nanoporous layer including nanopores is anodic aluminum oxide (AAO). The method of making the contact lens can include forming AAO on a flat substrate, such as glass. The method can include curing a backing layer film on the AAO, such as a polydimethylsiloxane (PDMS) film, to form a nanopore/backing layer composite film (e.g., AAO/PDMS composite film). The method can include removing the AAO/PDMS film from the glass substrate. The method can include placing the composite film on a backing lens, such that the backing layer contacts the backing lens, to form the contact lens. The backing lens can be formed from the same or similar material as the backing layer in the composite film, to facilitate physical bonding between the composite film and the backing lens (e.g., Van der Waals). In other embodiments, the backing lens and the backing layer in the composite film are formed from different materials.

EXAMPLES

Various embodiments of the present invention can be better understood by reference to the following Examples which are offered by way of illustration. The present invention is not limited to the Examples given herein.

Example 1. Formation of Contact Lens

Fabrication procedure involved two parts: backing lens fabrication and nanoporous film fabrication.

Backing lens fabrication is illustrated in FIG. 1A. PDMS was prepared with a volume ratio 9:1 to curing agent with thorough mixing and degassing for 2 hours. A chrome steel ball was then fixed on a preheated hotplate to 100° C. The PDMS mixture was poured onto the steel ball. The liquid PDMS slowly flowed down the ball due to gravity and high viscosity and cured for 3 minutes. After curing, a tube with circular rim was firmly pressed onto the ball to cut through PDMS, to obtain the backing lens, which had an appearance similar to a standard contact lens. The thickness was about 120 m at the edge and about 130 µm at the center.

Figure 1B:
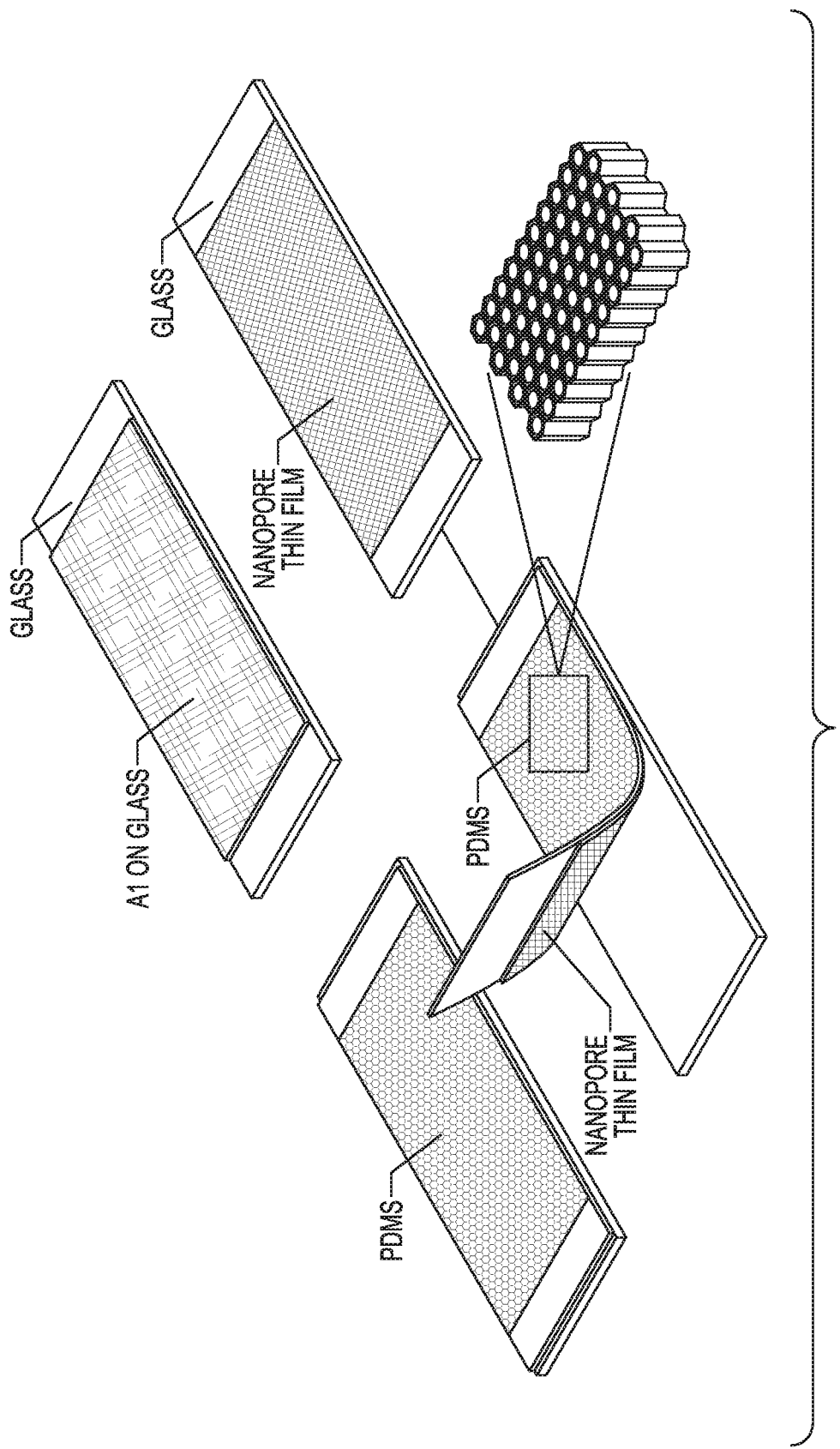
FIG. 1B illustrates nanoporous film fabrication, in accordance with various embodiments.

FIG. 1B illustrates fabrication of the nanoporous film. The cover glass slide was cleaned with acetone, iso-propyl alcohol (IPA) and de-ionized (DI) water, and then dehydrated with nitrogen gas. Highly purified aluminum was then deposited onto the cover glass slide with an e-beam evaporator. An electrochemical reaction in 5.8° C. 0.3M oxalic acid under 28 Volts for 3 hours transformed aluminum into anodic aluminum oxide (AAO). Typical AAO thickness was around 2 µm. A portion of the liquid PDMS mixture used in the backing lens fabrication was then poured onto the AAO/glass surface, followed by spinning AAO/glass at 3000 rpm for 30 seconds. The PDMS/AAO/glass was then baked at 65° C. for 3 hours to complete PDMS curing. Typical PDMS thickness were about 30 µm. In order to avoid AAO damage, scotch tape was attached to the PDMS surface in center area and the composite PDMS/AAO was gently peeled off. PDMS/AAO thin film obtained in this way generally had half-opened nanopores in the AAO side due to barrier layer formation against the glass during the electrochemical reaction. The PDMS/AAO composite film was thus treated with an etchant for 30 minutes at room temperature to complete pore opening process. The etchant was a mixture of 8% $H_3PO_4$ and 1.6% $H_2Cr_2O_3$ in water. The nanoporous PDMS/AAO composite film was then physically bonded to aforementioned PDMS backing lens to form smart contact lens device, using no adhesive, with direct contact of the PDMS backing lens to the PDMS/AAO composite film, which formed a secure connection that may have been enhanced by Van der Waals forces. The interface between the PDMS backing lens and the PDMS/AAO composite film could not be detected with the naked eye. The PDMS/AAO composite film on the backing lens was highly optically transparent. The pore depth was about 2 microns, the pore diameter was about 30 nm to about 50 nm, and the pore density was about $10^8$ to $10^{12}$ pores per $cm^2$. The pore depth and density was measured using a scanning electron microscope, and the pore depth was the thickness of the AAO film.

Example 2. Intraocular Pressure (IOP) Sensing

The contact lens was mounted on a cadaver pig's cornea. A light source and collector and a spectrophotometer was used to analyze the light reflected from the pores of the lens as the pressure in the eye was changed. The incident light from an LED was directed to the lens via an optical fiber probe and was reflected back to the same probe and sent to spectrophotometer. Under the changing pressure, the shape of nanopores and the interspace among the nanopores were changed and the incident angle of the illumination light from the optical fiber probe was changed; as a result, the optical interference fringes of the reflected optical signals from the nanopore thin film shifted.

To vary the pressure in the eye, an infusion bag filled with physiological saline solution was hung on a holder to provide tunable water pressure by adjusting bottle height on holder. Two syringe needles were penetrated into the pig eye at the limbus from both sides (at the 3- and 9-o'clock positions). One needle was connected with an infusion bag set to apply water pressure onto cornea, and the other was connected with pressure sensor and monitor to display real-time eye pressure induced by water pressure. The cadaver pig eye was lubricated with physiological saline solution before the contact lens was applied to it.

The optical fiber bundle was set up perpendicular to the contact lens to deliver illumination and collect reflection light, along with Ocean View installed PC to display and record reflection spectrum. Eye pressure was set to change from 10 mm Hg to 50 mm Hg back and forth with steps of 10 mmHg, by raising or reducing infusion bottle height on the holder, simultaneously monitored by pressure sensor and monitor. The reflection spectrum in the whole pressure changing process was collected and recorded.

Figure 2A:
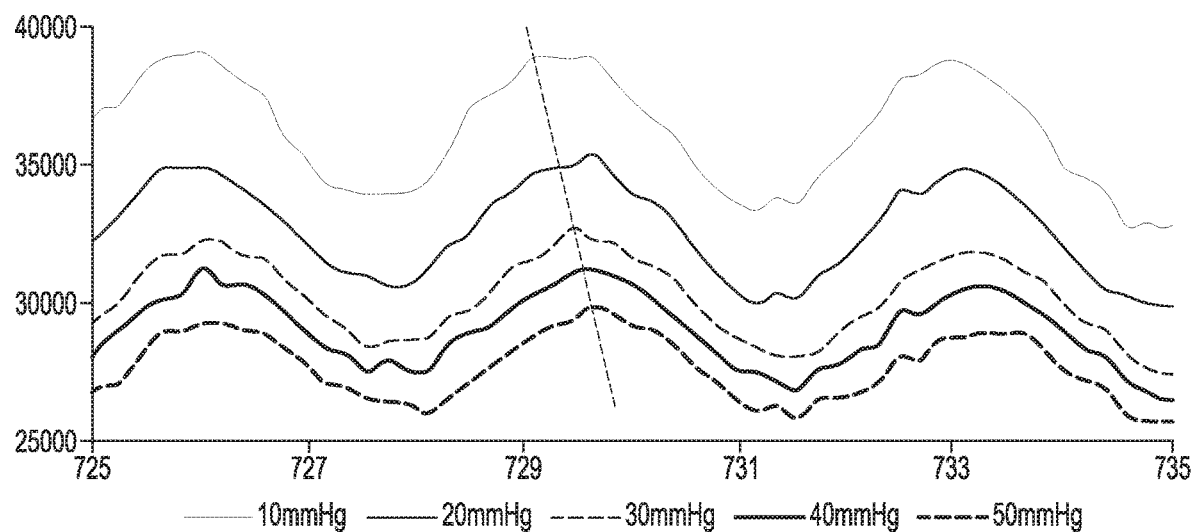
FIG. 2A illustrates intensity versus wavelength of reflections taken at various intraocular pressures, in accordance with various embodiments.
Figure 2B:
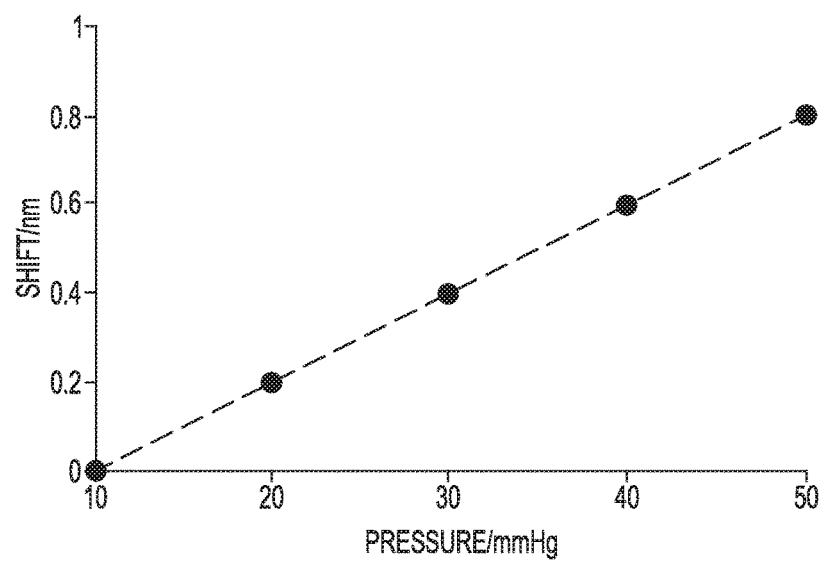
FIG. 2B illustrates the shift of the wavelength of reflected light versus the intraocular pressure, in accordance with various embodiments.

FIGS. 2A-B illustrate the results. FIG. 2A illustrates intensity versus wavelength of reflections taken at various intraocular pressures. FIG. 2B illustrates the correlation between the shift of the reflected wavelength to the intraocular pressure. By increasing the eye pressure from 10 mm Hg to 50 mm Hg, reflection spectrum peaks shifted to longer wavelength by 0.8 nm. By decreasing eye pressure from 50 mm Hg to 10 mm Hg, reflection spectrum peaks shifted to a shorter wavelength by 0.8 nm. The sensitivity was about 0.02 nm per mm Hg.

Example 3. Biomarker-Sensing

Recent studies indicate the mean concentration of cytokines IL-12p70 in tears is significantly lower for the diagnosed primary open-angle glaucoma (POAG) patients (3.94±2.19 pg/mL in control vs 2.31±1.156 pg/mL in POAG; P 0.035). This indicates measuring concentration of IL12p70 in the tear could verify the diagnosis of glaucoma. This Example demonstrates that the contact lens formed in Example 1 can be used to detect IL-12p70.

Sensing of biomarker was achieved by measuring an optical reflection signal from the contact lens because the biomarker's binding on sensor surface changed the optical path difference. The optical path difference was caused by the change of effective refractive index and thickness due to the binding of the biomarker. Such variation of the optical path resulting from biomarker binding can occur with or without the presence of nanopores.

Figure 3A:
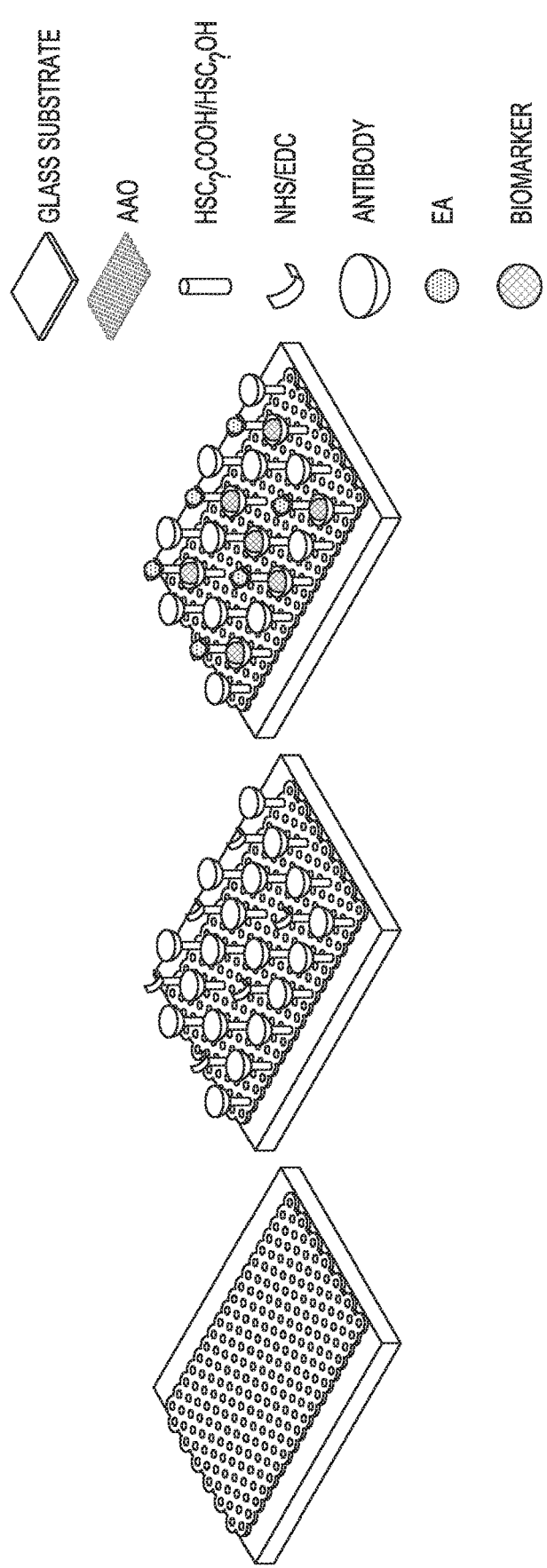
FIG. 3A illustrates surface functionalization of a nanoporous surface, in accordance with various embodiments.

FIG. 3A illustrates the functionalization of the nanoporous surface of the AAO/PDMS composite film. The nanoporous surface was coated with 10 nm Au using sputtering equipment and was functionalized with human IL-12p70 antibody through 1-ethyl-3-(3-dimethylaminopropyl) carbodiimide (EDC)/N-hydroxysulfosuccinimide (NHS) chemistry. The Au-coated sensor surface was immersed in 10 mM $HSC_{10}COOH/HSC_8OH$ overnight at 4° C. and then was washed with pure ethanol and Millipore DI water. After the surface was dried, the surface was immersed in a solution of NHS and EDC (NHS 0.2 M, EDC 0.05 M) for 2 hours. The sensor surface was washed with DI water and then immersed in the 5 μM antibody solution overnight. This was followed by loading 100 μL 1 M ethanolamine (EA) to block the non-occupied $HSC_{10}COOH/HSC_8OH$ sites activated by the EDC/NHS. Finally, the sensor surface was rinsed with PBS buffer to flush off non-specifically adsorbed proteins. At this stage, the sensor was ready for measurement.

Figure 3B:
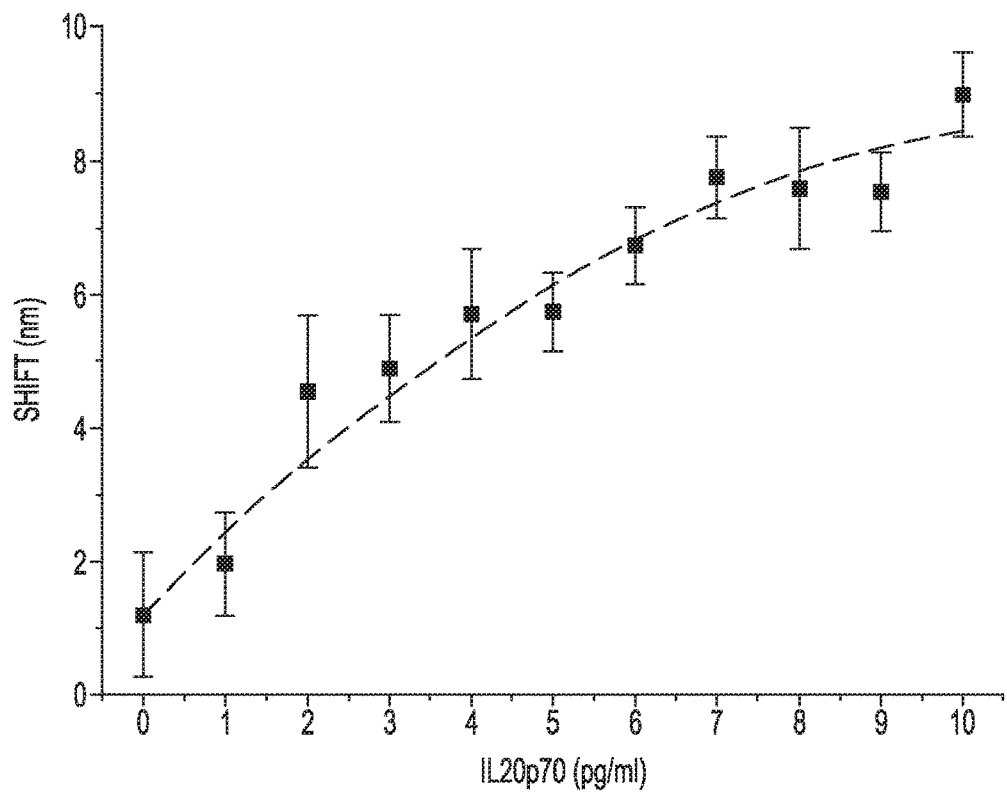
FIG. 3B illustrates the shift in wavelength of reflected light versus the concentration of IL20p70, in accordance with various embodiments.

Mouse IL-12 Protein diluted in artificial tears ranging from 0 pg/ml to 10 pg/ml was applied on the sensor surface for 2 hours incubation, and the optical signals were then measured. FIG. 3B illustrates the shift in wavelength of reflected light versus the concentration of IL20p70, showing that optical signal's fringes shifted with different IL20p70 concentrations. The peak shift of the optical signals increased from 1.2 nm to 9 nm when the concentration of IL-12p70 increased from 0 pg/ml to 10 pg/ml. This indicated a sensor sensitivity of 0.78 nm/(pg/ml) for detecting IL-12p70.

Example 4. Drug Release

The nanopores of the AAO/PDMS composite can be used for drug storage and for extended drug release. For example, one of drugs typically used for glaucoma is Timolol. In order to observe the extended drug release by the smart contact lens easily, fluorescein dye solution was utilized to mimic Timolol or another suitable drug releasing from the contact lens.

500 μl Fluorescein sodium saline diluted into 10 μg/ml was applied onto the contact lens surface of the contact lens of Example 1, allowing it to be diffused into the nanopores or deposited on the AAO surface. After sensor surface was completely dried, the contact lens was then immersed into DI water for specific time and a fluorescence image was taken with a microscope. A color filter was used to pass blue light as illumination for taking fluorescence images, since fluorescein dye has a maximum absorption at 494 nm and maximum emission at 512 nm. Fluorescence intensity of the AAO pattern was measured after being immersed into DI water for 2 hrs. 6 hrs, 10 hrs, 1 day, 2 day, 3 day, 5 day, 7 day, 14 day, 21 day, using a 2-second exposure time.

Quantified average fluorescence intensity across the same spot on the contact lens surface was measured.

Figure 4:
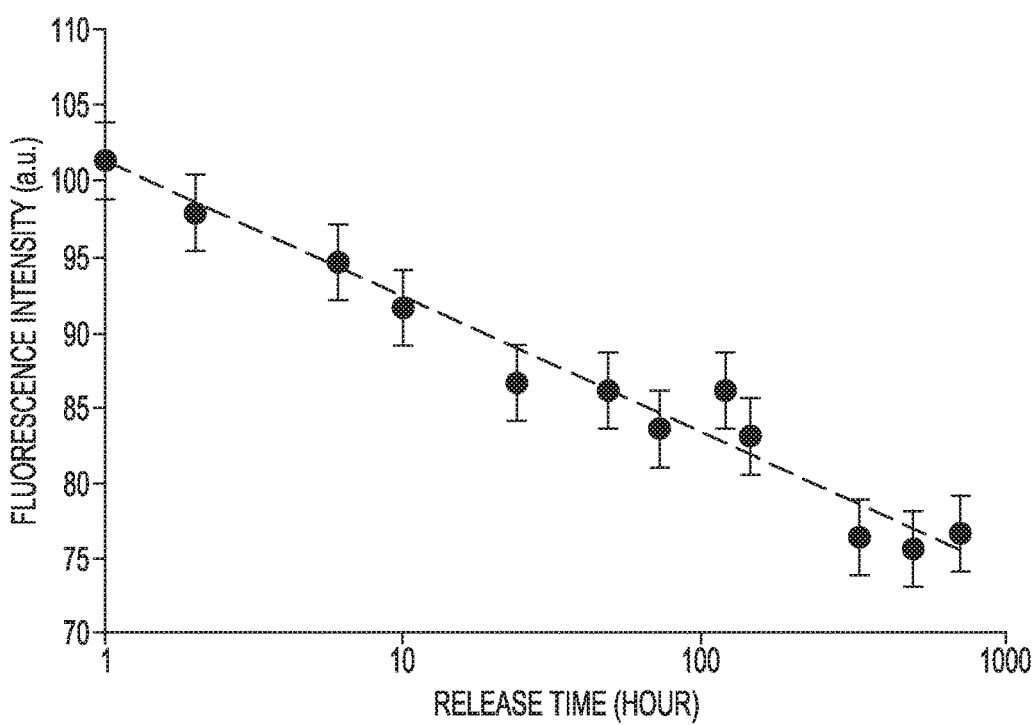
FIG. 4 illustrates fluorescence intensity versus release time, in accordance with various embodiments.

FIG. 4 illustrates the results, showing fluorescence intensity versus release time. Results show that with time increasing, fluorescence intensity decreased in logarithmic manner, indicating fluorescein dye release from AAO nanostructure into surrounding solution. Drug release could easily last as long as 21 days. These experiments indicate the nanopores inside the contact lens can be used as a drug storage and release device.

Example 5. Multifunctional Contact Lens

Figure 5C:
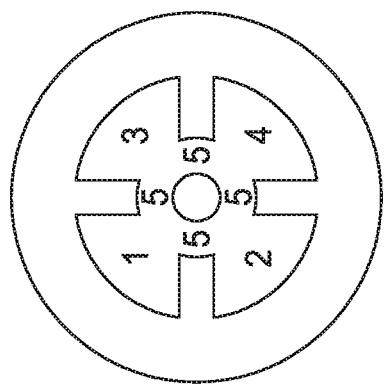
FIG. 5C illustrates a close-up front view of a contact lens on an eye, showing various regions thereon, in accordance with various embodiments.
Figure 5B:
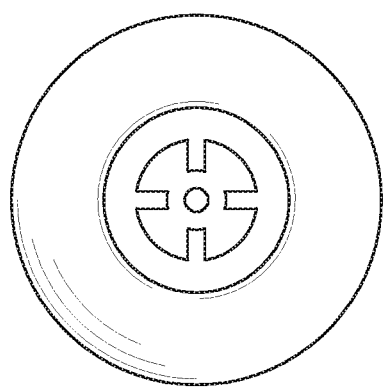
FIG. 5B illustrates a front view of a contact lens on an eye, in accordance with various embodiments.
Figure 5A:
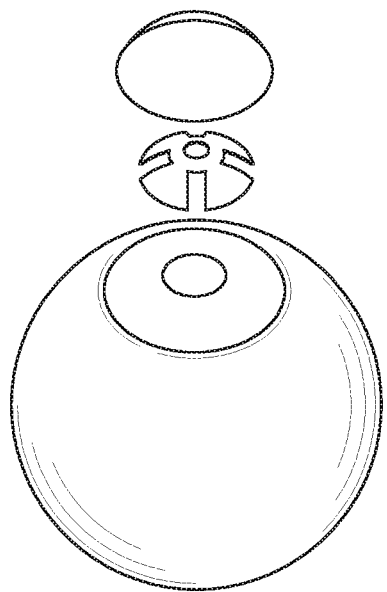
FIG. 5A illustrates a side view of a disassembled contact lens and an eye, in accordance with various embodiments.

Example 1 was repeated, but a 3D printed mold is utilized to fabricate the PDMS/AAO composite into a specific shape, as shown in FIG. 5A-C. Examples 3-4 were performed using the contact lens, installing biomarker sensors thereon and loading drugs into pores, in separate regions of the contact lens, leaving the central region open for intraocular pressure measurement. FIG. 5A illustrates a side view, showing the backing lens and the AAO/PDMS nanocomposite composite before bonding together and placing on the eye. FIG. 5B illustrates a front view of the contact lens on an eye. FIG. 5C illustrates a close-up front view of the lens, showing various regions thereon. Regions 1 4 included the biomarker sensors described in Example 3, regions 2 and 3 included drugs in the pores for drug release as described in Example 4, and region 5 could be used for intraocular pressure (IOP) measurement.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

EXEMPLARY EMBODIMENTS

The following exemplary embodiments are provided, the numbering of which is not to be construed as designating levels of importance:

Embodiment 1 provides a contact lens comprising:
a nanoporous film comprising nanopores that are on an inner surface of the contact lens; and
a backing lens on the nanoporous film.

Embodiment 2 provides the contact lens of Embodiment 1, wherein the nanopores are orthogonally-oriented with respect to the inner surface of the contact lens.

Embodiment 3 provides the contact lens of any one of Embodiments 1-2, wherein at least some of the nanopores comprise open ends on the inner surface of the contact lens.

Embodiment 4 provides the contact lens of any one of Embodiments 1-3, wherein at least some of the nanopores comprise closed ends on the inner surface of the contact lens.

Embodiment 5 provides the contact lens of any one of Embodiments 1-4, wherein the nanopores in the nanoporous film have a depth of about 0.1 micron to about 10 microns.

Embodiment 6 provides the contact lens of any one of Embodiments 1-5, wherein the nanopores in the nanoporous film have a depth of about 1 micron to about 3 microns.

Embodiment 7 provides the contact lens of any one of Embodiments 1-6, wherein the nanopores in the nanoporous film has a diameter of about 10 nm to about 200 nm.

Embodiment 8 provides the contact lens of any one of Embodiments 1-7, wherein the nanopores in the nanoporous film have a diameter of about 30 nm to about 50 nm.

Embodiment 9 provides the contact lens of any one of Embodiments 1-8, wherein the nanopores in the nanoporous film have a density of about $10^5$ to about $10^{15}$ pores per $cm^2$.

Embodiment 10 provides the contact lens of anyone of Embodiments 1-9, wherein the nanopores in the nanoporous film have a density of about $10^8$ to about $10^{12}$ pores per $cm^2$.

Embodiment 11 provides the contact lens of any one of Embodiments 1-10, wherein the nanoporous film comprises a metal, a metal oxide, or a combination thereof.

Embodiment 12 provides the contact lens of any one of Embodiments 1-11, wherein the nanoporous film comprises aluminum oxide.

Embodiment 13 provides the contact lens of any one of Embodiments 1-12, wherein the nanoporous film comprises anodic aluminum oxide (AAO).

Embodiment 14 provides the contact lens of any one of Embodiments 1-13, wherein the nanoporous film comprises a nanoporous layer comprising the nanopores, and a backing layer that contacts the backing lens.

Embodiment 15 provides the contact lens of Embodiment 14, wherein the nanoporous layer comprises a metal, a metal oxide, or a combination thereof.

Embodiment 16 provides the contact lens of any one of Embodiments 14-15, wherein the nanoporous layer comprises aluminum oxide.

Embodiment 17 provides the contact lens of anyone of Embodiments 14-16, wherein the nanoporous layer comprises anodic aluminum oxide (AAO).

Embodiment 18 provides the contact lens of any one of Embodiments 14-17, wherein the nanoporous layer has a thickness of about 0.1 micron to about 10 microns.

Embodiment 19 provides the contact lens of any one of Embodiments 14-18, wherein the nanoporous layer has a thickness of about 1 micron to about 3 microns.

Embodiment 20 provides the contact lens of any one of Embodiments 14-19, wherein the backing layer comprises polydimethylsiloxane (PDMS), poly(ethylene glycol) methacrylate (PEGMA), or a combination thereof.

Embodiment 21 provides the contact lens of anyone of Embodiments 14-20, wherein the backing layer comprises polydimethylsiloxane (PDMS).

Embodiment 22 provides the contact lens of any one of Embodiments 14-21, wherein the backing layer has a thickness of about 1 micron to about 100 microns.

Embodiment 23 provides the contact lens of anyone of Embodiments 14-22, wherein the backing layer has a thickness of about 20 microns to about 40 microns.

Embodiment 24 provides the contact lens of any one of Embodiments 1-23, wherein the nanoporous film has a thickness of about 1 micron to about 150 microns.

Embodiment 25 provides the contact lens of anyone of Embodiments 1-24, wherein the nanoporous film has a thickness of about 20 microns to about 45 microns.

Embodiment 26 provides the contact lens of any one of Embodiments 1-25, wherein the backing lens is attached to the nanoporous film.

Embodiment 27 provides the contact lens of any one of Embodiments 1-26, wherein the backing lens is adhered to the nanoporous film via adhesive.

Embodiment 28 provides the contact lens of anyone of Embodiments 1-27, wherein the backing lens directly contacts the nanoporous film without an intervening layer.

Embodiment 29 provides the contact lens of any one of Embodiments 1-28, wherein the backing lens is adhered to the nanoporous film via Van der Waals forces.

Embodiment 30 provides the contact lens of any one of Embodiments 1-29, wherein the backing lens is part of an outer surface of the contact lens.

Embodiment 31 provides the contact lens of any one of Embodiments 1-30, wherein the backing lens is configured to hold the nanoporous film against an eye wearing the contact lens.

Embodiment 32 provides the contact lens of any one of Embodiments 1-31, wherein the backing lens is configured to provide vision correction to an eye wearing the contact lens.

Embodiment 33 provides the contact lens of anyone of Embodiments 1-32, wherein the contact lens is configured to provide no vision correction to an eye that wears the contact lens.

Embodiment 34 provides the contact lens of any one of Embodiments 1-33, wherein the backing lens comprises polydimethylsiloxane (PDMS), poly(ethylene glycol) methacrylate (PEGMA), or a combination thereof.

Embodiment 35 provides the contact lens of any one of Embodiments 1-34, wherein the backing lens comprises polydimethylsiloxane (PDMS).

Embodiment 36 provides the contact lens of any one of Embodiments 1-35, wherein the backing lens has a thickness of about 50 microns to about 2 mm.

Embodiment 37 provides the contact lens of any one of Embodiments 1-36, wherein the backing lens has a thickness of about 100 microns to about 150 microns.

Embodiment 38 provides the contact lens of anyone of Embodiments 1-37, wherein the contact lens has a thickness of about 50 microns to about 50 microns to about 2,500 microns.

Embodiment 39 provides the contact lens of anyone of Embodiments 1-38, wherein the contact lens has a thickness of about 150 microns to about 170 microns.

Embodiment 40 provides the contact lens of any one of Embodiments 1-39, wherein light reflected from the nanopores has a shift in wavelength that correlates to an intraocular pressure of an eye wearing the contact lens.

Embodiment 41 provides the contact lens of any one of Embodiments 40, wherein nanopores in a central region of the contact lens reflect light with a shift in wavelength that correlates to the intraocular pressure.

Embodiment 42 provides the contact lens of any one of Embodiments 1-41, wherein a biomarker-sensing region of the nanoporous film comprises antibodies absorptive toward a biomarker on the inner surface of the contact lens.

Embodiment 43 provides the contact lens of Embodiment 42, wherein portions of the nanoporous film comprising the antibodies reflect light with a shift in wavelength that correlates to a degree of loading of the biomarker on the antibodies.

Embodiment 44 provides the contact lens of any one of Embodiments 42-43, wherein the antibodies absorptive to the biomarker are present on an edge region of the contact lens.

Embodiment 45 provides the contact lens of any one of Embodiments 42-44, wherein the biomarker-sensing region of the nanoporous film is substantially free of nanopores.

Embodiment 46 provides the contact lens of any one of Embodiments 42-45, wherein the biomarker-sensing region of the nanoporous film comprises nanopores.

Embodiment 47 provides the contact lens of any one of Embodiments 42-46, wherein the biomarker is indicative of a disease or condition.

Embodiment 48 provides the contact lens of any one of Embodiments 42-47, wherein the biomarker is cytokines IL-12p70f.

Embodiment 49 provides the contact lens of any one of Embodiments 42-48, wherein the antibody is absorptive toward a biomarker indicative of a disease or condition.

Embodiment 50 provides the contact lens of any one of Embodiments 42-49, wherein the antibody is human IL-12p70 antibody.

Embodiment 51 provides the contact lens of any one of Embodiments 42-50, wherein the antibody is functionalized to the nanoporous film on the inner surface of the contact lens via a linker group and optionally via a metal film.

Embodiment 52 provides the contact lens of anyone of Embodiments 42-51, wherein the antibody is functionalized to the nanoporous film on the inner surface of the contact lens via a gold film on the nanoporous film with 1-ethyl-3-(3-dimethylaminopropyl) carbodiimide (EDC)/N-hydroxysulfosuccinimide (NHS) chemistry.

Embodiment 53 provides the contact lens of any one of Embodiments 1-52, wherein at least some of the nanopores in a drug-storage region of the nanoporous film comprise a drug therein.

Embodiment 54 provides the contact lens of anyone of Embodiments 53, wherein the nanopores that comprise the drug are in an edge region of the nanoporous film.

Embodiment 55 provides the contact lens of any one of Embodiments 53-54, wherein the drug comprises a drug for ocular treatment.

Embodiment 56 provides the contact lens of any one of Embodiments 53-55, wherein the drug comprises timolol.

Embodiment 57 provides the contact lens of any one of Embodiments 53-56, wherein the nanopores comprising the drug comprise open ends on the inner surface of the contact lens.

Embodiment 58 provides the contact lens of any one of Embodiments 53-57, wherein at least some of the nanopores comprising the drug comprise a water-soluble cap or plug that at least partially blocks the end of the nanopores on the inner surface of the contact lens.

Embodiment 59 provides the contact lens of anyone of Embodiments 53-58, wherein the contact lens delivers the drug in an extended release pattern to an eye wearing the contact lens.

Embodiment 60 provides a contact lens comprising:
a nanoporous film comprising nanopores that are on an inner surface of the contact lens and that are orthogonally-oriented with respect to the inner surface of the contact lens, the nanoporous film comprising anodic aluminum oxide (AAO) on the inner surface of the contact lens; and
a backing lens on the nanoporous film that is configured to hold the nanoporous film against an eye wearing the contact lens, the backing lens comprising polydimethylsiloxane (PDMS).

Embodiment 61 provides the contact lens of Embodiment 60, wherein a biomarker-sensing portion of the nanoporous film is functionalized with human IL-12p70 antibody, the biomarker-sensing portion of the nanoporous film reflecting light with a shift in wavelength that correlates to a degree of loading of cytokines IL-12p70 on the antibodies.

Embodiment 62 provides the contact lens of any one of Embodiments 60-61, wherein at least some of the nanopores in a drug-storage region of the nanoporous film comprise timolol therein.

Embodiment 63 provides a method of using the contact lens of any one of Embodiments 1-62 in a wearer's eye, the method comprising:

exposing the contact lens to a light source;

measuring wavelength and intensity of light from the light source reflected from the contact lens in the wearer's eye; and determining intraocular pressure (IOP) from the wavelength and intensity of light measured.

Embodiment 64 provides a method of using the contact lens of any one of Embodiments 40-59 in a wearer's eye, the method comprising:

exposing the contact lens to a light source;

measuring wavelength and intensity of light from the light source reflected from the contact lens in the wearer's eye; and determining glaucoma biomarker concentration or change in concentration from the wavelength and intensity of light measured.

Embodiment 65 provides a method of using the contact lens of any one of Embodiments 51-59 in a wearer's eye, the method comprising:

providing the drug to the wearer's eye from the nanopores of the contact lens in the wearer's eye.

Embodiment 66 provides a method of making the contact lens of any one of Embodiments 1-62, the method comprising:

placing the nanoporous film on the backing lens, to form the contact lens.

Embodiment 67 provides the method of Embodiment 66, comprising forming a nanoporous layer comprising the nanopores on a flat substrate;

placing a backing layer on the nanoporous layer, to form the nanoporous film comprising the nanoporous layer and the backing layer; and removing the nanoporous film from the flat substrate.

Embodiment 68 provides the method of Embodiment 67, wherein the flat substrate is glass.

Embodiment 69 provides a method of making the contact lens of any one of Embodiments 1-62, the method comprising:

forming anodic aluminum oxide (AAO) on a glass substrate;

curing a polydimethylsiloxane (PDMS) film on the AAO, to form an AAO/PDMS composite film;

removing the AAO/PDMS composite film from the glass substrate; and placing the AAO/PDMS composite film on a backing lens, to form the contact lens.

Embodiment 70 provides the contact les or method of any one or any combination of Embodiments 1-69 optionally configured such that all elements or options recited are available to use or select from.

What is claimed is:

1. A contact lens comprising:

a nanoporous film comprising nanopores that are on an inner surface of the contact lens, wherein the nanoporous film comprises anodic aluminum oxide (AAO); and a backing lens on the nanoporous film.

2. The contact lens of claim 1, wherein the nanopores are orthogonally-oriented with respect to the inner surface of the contact lens.

3. The contact lens of claim 1, wherein the nanoporous film comprises a nanoporous layer comprising the nanopores, wherein the nanoporous layer comprises the AAO, and wherein the nanoporous film comprises a backing layer that contacts the backing lens.

4. The contact lens of claim 3, wherein the nanoporous layer has a thickness of about 0.1 micron to about 10 microns.

5. The contact lens of claim 3, wherein the backing layer comprises polydimethylsiloxane (PDMS), poly(ethylene glycol) methacrylate (PEGMA), or a combination thereof.

6. The contact lens of claim 3, wherein the backing layer has a thickness of about 1 micron to about 100 microns.

7. The contact lens of claim 1, wherein the nanoporous film has a thickness of about 1 micron to about 150 microns.

8. The contact lens of claim 1, wherein the backing lens is configured to hold the nanoporous film against an eye wearing the contact lens.

9. The contact lens of claim 1, wherein light reflected from the nanopores has a shift in wavelength that correlates to an intraocular pressure of an eye wearing the contact lens.

10. The contact lens of claim 1, wherein a biomarker-sensing region of the nanoporous film comprises antibodies absorptive toward a biomarker on the inner surface of the contact lens, wherein portions of the nanoporous film comprising the antibodies reflect light with a shift in wavelength that correlates to a degree of loading of the biomarker on the antibodies.

11. The contact lens of claim 10, wherein the biomarker is cytokines IL-12p70f.

12. The contact lens of claim 10, wherein the antibody is human IL-12p70 antibody.

13. The contact lens of claim 1, wherein at least some of the nanopores in a drug-storage region of the nanoporous film comprise a drug therein.

14. A contact lens comprising:

a nanoporous film comprising nanopores that are on an inner surface of the contact lens and that are orthogonally-oriented with respect to the inner surface of the contact lens, the nanoporous film comprising anodic aluminum oxide (AAO) on the inner surface of the contact lens; and a backing lens on the nanoporous film that is configured to hold the nanoporous film against an eye wearing the contact lens, the backing lens comprising polydimethylsiloxane (PDMS).

15. A method of using the contact lens of claim 1 in a wearer's eye, the method comprising:

exposing the contact lens to a light source;

measuring wavelength and intensity of light from the light source reflected from the contact lens in the wearer's eye; and determining intraocular pressure (IOP) from the wavelength and intensity of light measured.

16. A method of using the contact lens of claim 10 in a wearer's eye, the method comprising:

exposing the contact lens to a light source;

measuring wavelength and intensity of light from the light source reflected from the contact lens in the wearer's eye; and determining glaucoma biomarker concentration or change in concentration from the wavelength and intensity of light measured.

17. A method of using the contact lens of claim 13 in a wearer's eye, the method comprising:
  providing the drug to the wearer's eye from the nanopores of the contact lens in the wearer's eye.

18. A method of making the contact lens of claim 1, the method comprising:
  placing the nanoporous film on the backing lens, to form the contact lens.

* * * * *